United States Patent [19]

Mettler

[11] Patent Number: 4,827,015

[45] Date of Patent: May 2, 1989

[54] PROCESS FOR THE PRODUCTION OF AMINOMALONIC ACID DINITRILE SALTS

[75] Inventor: Hanspeter Mettler, Brig-Glis, Switzerland

[73] Assignee: Lonza Ltd., Gampel, Switzerland

[21] Appl. No.: 201,166

[22] Filed: Jun. 2, 1988

[30] Foreign Application Priority Data

Jun. 9, 1987 [CH] Switzerland ............... 2167/87

[51] Int. Cl.$^4$ ............................................. C07C 121/22
[52] U.S. Cl. .................................................. 558/453
[58] Field of Search ....................................... 558/453

[56] References Cited

U.S. PATENT DOCUMENTS 3,670,007 6/1972 Ferris ...................... 558/453
4,212,818 7/1980 Junek et al. ............... 558/453 X

FOREIGN PATENT DOCUMENTS 0003335 8/1929 European Pat. Off. ............ 558/453

OTHER PUBLICATIONS

Weygand/Hilgetag, "Preparations Organic Chemistry", (1972), p. 564, –John Wiley & Sons, N.Y., London, Sydney, Toronto.
Ferris et al., J. Am. Chem. Soc., 87, (1965), pp. 4976–4977.
Ferris et al., J. Am. Chem. Soc., 88, (1966), pp. 3829–3831.
J. P. Ferris, R. A. Sanchez and R. W. Mancuso, Org. Synth. 48, 1–3 (date unknown).

*Primary Examiner*—Joseph Paul Brust
*Attorney, Agent, or Firm*—Fisher, Christen & Sabol

[57] ABSTRACT

Process for the production of aminomalonic acid dinitrile salts from malonic acid dinitrile by the hydrogenation of its oximation product.

18 Claims, No Drawings

PROCESS FOR THE PRODUCTION OF AMINOMALONIC ACID DINITRILE SALTS

BACKGROUND OF THE INVENTION

1. Field of the Invention

The invention relates to a process for the production of aminomalonic acid dinitrile salts.

2. Background Art

It is well known to isolate aminomalodinitrile as p-toluenesulfonate by the reduction of oximinomalonic acid dinitrile with aluminum amalgam. But this production is protracted and complicated. Amalgamation of the aluminum causes difficulties, since the mercury layer does not adhere well to the surface of the aluminum. Moreover, much of the product remains in the precipitate when the aluminum hydroxide is suctioned off after the reduction [J. P. Ferris and L. E. Orgel, J. Am. Chem. Soc. 87, 4976-7 (1965); J. P. Ferris and L. E. Orgel, J. Am. Chem. Soc. 88, 3829-31 (1966); J. P. Ferris, U.S. Pat. No. 3,670,007 (1972), C.A. 77, 100866v (1972); J. P. Ferris, R. A. Sanchez and R. W. Mancuso, Org. Synth. 48, 1-3]. In U.S. Pat. No. 3,670,007, J. P. Ferris also describes reductions with zinc and sodium dithionite, but limits himself to the qualitative proof of aminomalonic acid dinitrile in the reaction solution.

A process is also known, in which oximinomalonic acid dinitrile is reacted in the presence of Raney catalysts as the reduction agent at hydrogen pressures of 5 to 7 bars (4 to 6 ata) and temperatures of 10° to 80° C. in tetrahydrofuran as the solvent. The aminomalonic acid dinitrile is precipitated from the reaction solution by treatment with p-toluenesulfonic acid and is isolated as tosylate or reacted in acetic anhydride as the solvent to aminomalonic acid dinitrile. The latter is precipitated and is isolated as acetyl aminomalonic acid dinitrile (European Published patent application No. 3353). According to such process yields of 27 to 49 percent are obtained.

BROAD DESCRIPTION OF THE INVENTION

The object of the invention is to provide an improved process by which substantially higher yields result than the yields achieved in European Published patent application No. 3335. This object is achieved by the invention process.

The invention involves a process for the production of aminomalonic acid dinitrile salts by the hydrogenation of oximinomalonic acid dinitrile and the isolation of the aminomalonic acid dinitrile as an acid salt. The malonic acid dinitrile at a pH of 3.8 to 4.2 is nitrosated in a mixture of $H_2O/H_2SO_4$. The nitrosation product is extracted with a solvent which is not miscible with water. The hydrogenation is performed in a polar solvent in the presence of a noble metal catalyst at hydrogen pressures of 1 to 40 bars and temperatures of 10° to 50° C. The aminomalonic acid dinitrile is precipitated from the reaction mixture by treatment with an acid and is isolated as the acid salt.

Nitrosation of the malonic acid dinitrile is performed at a pH of 3.8 to 4.2, preferably 4, in a mixture of $H_2O/H_2SO_4$, suitably with sodium nitrite. This mixture of $H_2O/H_2SO_4$ preferably consists of 15 to 30 moles of water and 0.02 to 0.05 mole of sulfuric acid, relative to 1 mole of malonic acid dinitrile. The temperature advantageously is 15° to 25° C.

The reaction mixture resulting after nitrosation is advantageously extracted after the addition of 0.5 to 1.0 mole of sulfuric acid per mole of malonic acid dinitrile used.

The extraction of the nitrosation product can be performed with methylene chloride, dimethyl ether or ethyl acetate. The hydrogenation takes place in a polar organic solvent, suitably in ethanol, ether, tetrahydrofuran or ethyl acetate. The solvent can be used alone or in combination with an organic acid, such as acetic acid, formic acid and toluenesulfonic acid, or an inorganic acid, such as, hydrochloric acid, phosphoric acid and sulfuric acid.

According to a preferred procedure the same solvent is used for both the extraction and hydrogenation steps. Ethyl acetate is particularly suitable for this preferred procedure.

Advantageously for the extraction, 15 to 30 moles, preferably 20 moles, of ethyl acetate is used per mole of malonic acid dinitrile used.

The extraction solution containing the oximation product is adjusted to a molar ratio of acetic acid/ethyl acetate of 2:1 to 15:1 with acetic and then fed to the hydrogenation. In this case, it is has proved advisable to remove a part of the ethyl acetate and then to add the necessary acetic acid (as 100 percent).

The hydrogenation catalyst is a noble metal catalyst. Such catalysts are, for example, platinum, palladium or rhodium, which are usually applied on a support, preferably on carbon. It is also possible to use $PtO_2$. Preferably platinum is used in a concentration of 1 to 10 percent, advantageously 5 percent, applied on carbon. In a suitable embodiment, 8 to 30 g, preferably 15 g, of catalyst is used per mole of malonic acid dinitrile used. After the hydrogenation, the reaction mixture is suitably filtered.

After that, the corresponding acid, suitably methanesulfonic acid, p-toluenesulfonic acid or concentrated hydrochloric acid, is added to the filtrate containing the aminomalonic acid dinitrile.

As a rule, the corresponding acid salt can be precipitated and, after that, isolated after partial concentration of the reaction solution and by means of the addition of an apolar organic solvent, such as, toluene.

Optionally, the hydrochloric acid can be subjected to an additional purification by recrystallization.

DETAILED DESCRIPTION OF THE INVENTION

Example 1

Production of aminomalonic acid dinitrile p-toluene-sulfonate 13.8 g (0.200 mole) of sodium nitrite in 40 g of water was added to 13.2 g (0.200 mole) of malonic acid dinitrile (MDN) in 60 g of water in 30 minutes at 20° C. In this case, the pH of the solution was kept constant at 4 by the addition of sulfuric acid. The solution was stirred for 4 hours at 20° C., mixed with 70 g of 20 percent sulfuric acid and extracted with 4×90 g of ethyl acetate. The organic phase was dried for 2 hours on sodium sulfate and concentrated to 150 g. This phase containing the hydroximinomalonic acid dinitrile was mixed with 250 g of acetic acid and hydrogenated at 10 bars of hydrogen pressure and room temperature on 3.0 g of Pt/C (5 percent). The reaction mixture was filtered. The filtrate was mixed with 38.0 g (0.200 mole) of p-toluenesulfonic acid, concentrated to a total of 280 g, mixed with 600 g of toluene and allowed to stand for 12 hours at 4° C. The precipitated aminomalonic acid dinitrile p-toluenesulfonate was filtered off, washed with toluene and dried. The yield of the product was 44.93 g (74.9 percent of theory). The melting point of the product was 163.5° to 163.8° C. After recrystallization from ethanol, a product with a melting point of 167.0° to 168.0° C. was obtained.

Example 2

Production of aminomalonic acid dinitrile methanesulfonate

A solution of 4.76 g (0.050 mole) of hydroximinomalonic acid dinitrile in 38 g of ethyl acetate (produced as described in Example 1) was mixed with 60 g of acetic acid and hydrogenated at 10 bars of hydrogen pressure and room temperature on 0.8 g Pt/C (5 percent). The reaction mixture was filtered. The filtrate was mixed with 4.81 g (0.050 mole) of methanesulfonic acid, concentrated to 74 g, mixed with 175 g of toluene and allowed to stand for 12 hours at 4° C. The precipitated aminomalonic acid dinitrile methanesulfonate was filtered off, washed with toluene and dried. 8.43 g of the product was obtained in a yield of 83.3 percent (relative to hydroximinomalonic acid dinitrile). The product with a melting point of 149° to 151° C. was isolated by recrystallization from ethanol. The following is data concerning the product:

NMR: (300 MHz, DMSO-d$^6$) 7.85 (s, 3H), 6.10 (s, 2H), 2.49 (s, 3H).

Example 3

Production of aminomalonic acid dinitrile hydrochloride

A solution of 4.76 g (0.050 mole) of hydroximinomalonic acid dinitrile in 38 g of ethyl acetate (produced as described in Example 1) was mixed with 60 g of acetic acid and hydrogenated at 10 bars of hydrogen pressure and room temperature on 0.08 g Pt/C (5 percent). The reaction mixture was filtered. The filtrate was mixed with 7.33 g (0.075 mole) of concentrated hydrochloric acid, concentrated to 65 g, mixed with 175 g of toluene and allowed to stand for 12 hours at 4° C. The precipitated aminomalonic acid dinitrile hydrochloride was filtered off, washed with toluene and dried. 4.10 g of the product was obtained in a yield of 63.4 percent (relative to hydroximinomalonic acid dinitrile). The product melting point: Decomposition starting at about 160° C. The following is data concerning the product:

NMR: (300 MHz, DMSO-d$^6$) 8.25 (s, 3H), 6.34 (s, 1H).

What is claimed is:

1. Process for the production of an aminomalonic acid dinitrile salt by the hydrogenation of hydroxyiminomalonic acid dinitrile and the isolation of the aminomalonic acid dinitrile as an acid salt, characterized in that malonic acid dinitrile at a pH of 3.8 to 4.2 is nitrosated in the presence of a nitrosation agent in a mixture of $H_2O/H_2SO_4$, the nitrosation product is extracted with a solvent which is not miscible with water, the hydrogenation is performed in a polar solvent in the presence of a noble metal catalyst at a hydrogen pressure of 1 to 40 bars and a temperature of 10° to 50° C., and the aminomalonic acid dinitrile is precipitated from the reaction mixture by treatment with an acid, said acid being capable of forming an acid salt with said aminomalonic acid dinitrile, and is isolated as the acid salt.

2. Process according to claim 1 wherein the nitrosation is performed with sodium nitrite as the nitrosation agent in a mixture of 15 to 30 moles of water and 0.02 to 0.05 mole of $H_2SO_4$, relative to 1 mole of malonic acid dinitrile.

3. Process according to claim 2 wherein the same solvent is used for the extraction and the hydrogenation.

4. Process according to claim 3 wherein ethyl acetate is used as the extraction agent and as the solvent for the hydrogenation.

5. Process according to claim 4 wherein the hydrogenation is performed in a mixture of ethyl acetate and acetic acid.

6. Process according to claim 5 wherein the hydrogenation is performed in a mixture of acetic acid and ethyl acetate in a molar ratio of 2 to 15 moles of acetic acid to 1 mole of ethyl acetate.

7. Process according to claim 6 wherein platinum on a carbon support is used as the noble metal catalyst.

8. Process according to claim 7 wherein methanesulfonic acid, p-toluenesulfonic acid or hydrochloric acid is used as the acid.

9. Process according to claim 1 wherein the same solvent is used for the extraction and the hydrogenation.

10. Process according to claim 1 wherein ethyl acetate is used as the extraction agent and as the solvent for the hydrogenation.

11. Process according to claim 1 wherein the hydrogenation is performed in a mixture of ethyl acetate and acetic acid.

12. Process according to claim 1 wherein the hydrogenation is performed in a mixture of acetic acid and ethyl acetate is a molar ratio of 2 to 15 moles of acetic acid to 1 mole of ethyl acetate.

13. Process according to claim 1 wherein platinum on a carbon support is used as the noble metal catalyst.

14. Process for the production of an aminomalonic acid dinitrile salt by the hydrogenation of hydroxyiminomalonic acid dinitrile and the isolation of the aminomalonic acid dinitrile as an acid salt, characterized in that malonic acid dinitrile at a pH of 3.8 to 4.2 is nitrosated in the presence of a nitrosation agent in a mixture of $H_2O/H_2SO_4$, the nitrosation product is extracted with a solvent which is not miscible with water, the hydrogenation is performed in a polar solvent in the presence of a noble metal catalyst at a hydrogen pressure of 1 to 40 bars and a temperature of 10° to 50 C., and the aminomalonic acid dinitrile is precipitated from the reaction mixture by treatment with an acid, said acid being selected from the group consisting of methanesulfonic acid, p-toluenesulfonic acid and hydrochloric acid, and is isolated as the acid salt.

15. Process as claimed in claim 1 wherein the nitrosation step is conducted at a temperature of 15° to 25° C.

16. Process as claimed in claim 2 wherein the nitrosation step is conducted at a temperature of 15° to 25° C.

17. Process as claimed in claim 1 wherein the noble metal catalyst is platinum, palladium or rhodium.

18. Process as claimed in claim 2 wherein the noble metal catalyst is platinum, palladium or rhodium.

* * * * *